(12) United States Patent
Angle et al.

(10) Patent No.: US 7,214,516 B2
(45) Date of Patent: May 8, 2007

(54) BACTERIAL EFFECTS ON METAL ACCUMULATION BY PLANTS

(75) Inventors: Jay Scott Angle, Ellicott City, MD (US); Rufus L. Chaney, Beltsville, MD (US); Reda Abdelaziz Abou-Shanab, Alexandria (EG); Peter Van Berkum, Columbia, MD (US)

(73) Assignee: University of Maryland, College Park, MD (US)

( * ) Notice: Subject to any disclaimer, the term of this patent is extended or adjusted under 35 U.S.C. 154(b) by 257 days.

(21) Appl. No.: 10/814,788

(22) Filed: Apr. 1, 2004

(65) Prior Publication Data
US 2005/0217174 A1  Oct. 6, 2005

(51) Int. Cl.
*C12P 3/00* (2006.01)
*C02F 3/32* (2006.01)
*C22B 19/00* (2006.01)
*C22B 15/00* (2006.01)

(52) U.S. Cl. .................. 435/168; 47/58.1 R; 75/710; 75/711; 75/712; 210/602; 210/681; 210/682; 435/262

(58) Field of Classification Search ............... 435/168, 435/262; 47/58.1 R; 75/711, 712; 210/602, 210/681, 682
See application file for complete search history.

(56) References Cited

U.S. PATENT DOCUMENTS

| | | | | |
|---|---|---|---|---|
| 5,711,784 A | * | 1/1998 | Chaney et al. | 75/712 |
| 5,785,735 A | * | 7/1998 | Raskin et al. | 75/711 |
| 5,917,117 A | * | 6/1999 | Ensley et al. | 75/711 |
| 5,944,872 A | * | 8/1999 | Chaney et al. | 75/712 |
| 6,159,270 A | * | 12/2000 | Raskin et al. | 75/711 |
| 6,786,948 B1 | * | 9/2004 | Chaney et al. | 435/168 |
| 2003/0140670 A1 | * | 7/2003 | Leggo | 71/15 |

* cited by examiner

*Primary Examiner*—Herbert J. Lilling
(74) *Attorney, Agent, or Firm*—Sqire, Sanders & Dempsey L.L.P

(57) ABSTRACT

The invention includes methods for (1) extracting metals from soil by the use of plants that extract and accumulate the metal and adding bacteria to the soil that enhances the ability of the plants to extract the metal, and (2) preparing soil for extraction of a metal by plants by adding bacteria to the soil that enhances the ability of plants to extract the metal. It is preferred that the plants be planted in the soil as seeds and that the bacteria added to the soil is also added to the seeds prior to planting.

49 Claims, 1 Drawing Sheet

BACTERIAL EFFECTS ON METAL ACCUMULATION BY PLANTS

DESCRIPTION OF THE INVENTION

1. Field of the Invention

The present invention relates to enhancing the ability of certain plants to extract metals from soil, particularly by adding bacteria to the soil.

2. Background of the Invention

Incorporated herein by reference to generally explain the nature of the art are the following: (1) Barber DA, Lee RB (1974), The effect of microorganisms on the absorption of manganese by plants. *New Phytology* 73: 97–106; (2) Chaney R L (1983), Plant uptake of inorganic waste constituents. In: Parr J F, Marsh P B, Kla J M, eds. *Land treatment of hazardous wastes*. Park Ridge, N.J., USA: Noyes Data Corporation, 50–76; (3) Salt DE, Krämer U (2000), Mechanisms of metal hyperaccumulation in plants. In: Raskin I, Ensley BD, eds. *Phytoremediation of toxic metals: using plants to clean up environment*. Sommerset, N.J., USA: John Wiley and Sons, Ltd., 231–246; (4) Kelley B C, Tuovinen (1988), Microbial oxidation of minerals in mine tailings. In: Solomons W, Foerstner V, eds, *Chemistry and biology of solid waste*. Berlin, Germany: Springer Verlag, 33–53; (5) Lynch J M, (1990), The *rhizosphere*. New York, USA: John Wiley and Sons; (6) Martin J P, Farmer W J, Ervin J O (1973), Influence of steam treatment and fumigation of soil on growth and elemental composition of avocado seedlings. *Soil Science Society of America* 37: 56–60; (7) Crowley D E, Wang Y C, Reid C P P, Szaniszlo P J (1991), Mechanisms of iron acquisition from siderophores by microorganisms and plants. *Plant and Soil* 130: 179–198; (8) Smith S E, Read D J (1997), *Mycorrhirazal symbiosis*. San Diego, Calif., USA: Academic Press; (9) Loper E J, Henkels, M D (1999), Utilization of heterologous siderophores enhances levels of iron available to *Pseudomonas putida* in the rhizosphere. *Applied Environmental Microbiology* 65: 5357–5363; (10) Nautiyal C S. (1999), An efficient microbiological growth medium for screening phosphate solubilizing microorganisms. *FEMS Microbiological Letters* 170:265–270; (11) Burd G I, Dixon D G, Glick B R (2000), Plant growth-promoting bacteria that decrease heavy metal toxicity in plants. *Canadian Journal of Microbiology* 46: 237–245; (12) Guan L L, Kanoh K Kamino K (2001), Effect of exogenous siderophores on iron uptake activity of marine bacteria under iron-limited conditions. *Applied Environmental Microbiology* 67: 1710–1717; (13) Wenzel W W, Jockwer F (1999), Accumulation of heavy metals in plants grown on mineralized soils of the Austrian Alps. *Environmental Pollution* 104:145–155; (14) Lasat M M (2002), Phytoextraction of toxic metals: a review of biological mechanisms. *Journal of Environmental Quality* 31: 109–120; (15) Ghaderian M Y S, Anthony J E L, Baker A J M, Baker (2000), Seedling mortality of metal hyperaccumulator plants resulting from damping off by Pythium spp. *New Phytology* 146:219–224; (16) Schlegel H G, Cosson J P, Baker A J M (1991), Nickel-hyperaccumulating plants provide a niche for nickel-resistant bacteria. *Botany Acta* 104: 18–25; (17) (Brooks et al., 1977) Baker A J M, McGrath S P, Reeves R D, Smith J A C. (2000), Metal hyperaccumulator plants: a review of the ecology and physiology of a biological resource for phytoremediation of metal-polluted soils; (18) Baker A J M, Brooks R. R. (1989), Terrestrial higher plants which hyperaccumulace metallic elements: a review of their distribution, ecology and phytochemistry. Biorecovery 1: 81–126; (19) Beyers BR, Powell M V, Lankfort CE (1967), Iron-chelating hydroxamic acid (schizoken) active in initiation of cell division in *Bacillus megaterium*. *Journal of Bacteriology* 93: 286–294; (20) Brooks R R, Lee J., Reeves R D, Jaffre T (1977), Detection of nickeliferous rocks by analysis of herbarium specimens of indicator plants. *Journal of Geochemistry and Explor* 7: 49–77; (21) Burd G I, Dixon D G, Glick B R (2000), Plant growth-promoting bacteria that decrease heavy metal toxicity in plants, Canadian *Journal of Microbiology* 46: 237–245; (22) Phytoextraction of soil nickel using *Alyssum* species, In: Parr J F, Marsh P B, KIa JM, eds. *Land treatment of hazardous wastes*, Park Ridge, N.J., USA, Noyes Data Corporation, 50–76; (22) Phytoextraction of soil nickel using *Alyssum* species, In: Wentzel W W, Adriano D C, Alloway B, Doner H E, Keller C, Lepp N W, Mench M. Naidu R, Pierzynski G M, eds. *Proceedings of the Extended Abstracts from the 5$^{th}$ International Conference on the Biochemistry of Trace Elements* (July 11–15, (1999), Vienna, Austria), Vienna, Italy: International Society of Trace Element Research, 14–15; (23) Ferriss R S, 1984, Effects of microwave oven treatment on microorganisms in soil, *Phytopathologyl* 74: 121–126; (24) Fletcher C L, Kaufman D D, (1980), Effects of sterilization methods on 3-chloronailine behavior in soul, *Journal of Agriculture Food Chemistry* 28: 667–671; (25) (Zn, Cd, Ni en al) en siderofoot-afhankelijke ijzer-opaname in verchillende flourescerende *Pseudomonas stamen*, Brussels, Belgium: Licentiaatsthesis, Departement Algemene Biologie; (26) Hassan MET, (1996), *Genetic mechanism of heavy metal resistance of Pseudomonas aeruginosa* CMG103, PhD thesis, University of Karachi, Pakistan; (27) Hu X, Boyer GL (1996), Siderophore-mediated aluminum uptake by *Bacillus megaterium* ATCC 19213, *Applied Environmental Microbiology* 62: 4044–4048; (28) Huyer M, Page W (1988), $Zn^{2+}$ increases siderophore production in Azotobacter vinelandii, *Applied Environmental Microbiology* 54: 2615–2631; (29) Kukier U, Chaney RL (2001), Amelioration of Ni phytotoxicity in muck and mineral soils, *Journal of Environmental Quality* 30: 1949–1960; (30) Lasat M M (2002), Phytoextraction of toxic metals, a review of biological mechanisms, *Journal of Environmental Quality* 31: 109–120; (31) Lopes A S, Wollum A G (1976) Comparative effects of methyl bromide, propylene oxide, and autoclave sterilization on specific soil chemical characteristics, *Turialba* 26: 351–355; 32) Neilands J B (1981), Microbial iron compounds, *Annual Review of Biochemistry* 50: 715–731; (33) Official Anal. Chem. (AOAC) Method (1984), 3 014(a), 14$^{th}$ edn. Gaithersberg, M D, USA: AOAC International, 38–40; (34) Peterson G H (1962), Microbial activity in heat and electron-sterilized soil seeded with microorganisms, *Canadian Journal of Microbiology* 8: 519–524; (35) Reasoner D J, Geldreich E E (1985), A new medium for the enumeration and subculture of bacteria from potable water, *Applied Environmental Microbiology* 49: 1–7; (36) Salt D E, Blaylock M, Kumar NPBA, Dushenkov V, Ensley B D, Chet I, Raskin I (1995), Phytoremediation: a novel strategy for the removal of toxic metals from the environment using plants, *Bio/Technology* 13: 468–474; (37) Skipper H D, Westermann D T (1973), Comparative effects of propylene oxide, sodium azide, and autoclaving on selected soil properties, *Soil Biological Biochemistry* 5: 409–414; (38) Whiting S N, De-Souza M P, Terry N (2001), Rhizosphere bacteria mobilize Zn for hyperaccumulation by *Thlaspi caerulescens*, *Environmental Science Technology* 35: 3144–3150; (39) Wolf D C, Dao T H, Scott H D, Lavy T L (1989), Influence of sterilization methods on selected soil microbiological, physical, and chemical properties, *Journal of Environmental Quality* 18: 39–44; and (40) Zhao F J, Hamon R E, McLaughlin M J (2001), Root exudates of the hyperaccumulator *Thalaspi caerulescens* do not enhance metal mobilization, *New Phytologist* 151: 613–620.

The following U.S. patents are also incorporated herein by reference to show the state of the art: U.S. Pat. No. 5,944,872 to Chaney, et al. entitled Method for Pytomining_Nickel, Cobalt and Other Metals from Soil and U.S. Pat. No. 5,711,784 to Chamy, et al. also entitled Method for Pytomining of Nickel, Cobalt and other Metals from Soil.

A number of plant species are capable of accumulating concentrations of metals from soil, and such known plant species are endemic to metalliferous soils. Among the metals that can be accumulated in plants are nickel, zinc and cobalt and certain plants can accumulate these metals in their above ground biomass at levels greatly exceeding those normally considered to be phytotoxic. Such plants are termed metal "hyperaccumulators." In the case of nickel (chemical symbol, "Ni"), hyperaccumulators are characterized by being able to accumulate concentrations greater than 1000 mg of Ni $kg^{-1}$ of shoot dried weight when such plants are grown in their natural habitat. More than 400 plant species have been identified as hyperaccumulators, of which 75% are Ni hyperaccumulators that grow on ultramafic soils.

As a result of their ability to remove considerable quantities of metals from soils, hyperaccumulators are attracting interest from scientists interested in phytoremediation (also more generally called phytoextraction), which could be a cost-effective technique for decontamination of environments polluted by metals. Phytoremediation involves planting hyperaccumulators in soil contaminated with metal, or growing hyperaccumulators from seeds in the contaminated soil, and allowing the plants to extract the metal. The Ni-hyperaccumulating plant *Alyssum murale* has received the most attention because of its extraordinary ability to extract and accumulate Ni from soils.

Hyperaccumulation of metals by some plants has been extensively investigated. Most of the research on hyperaccumulation has focused on the physiological mechanisms of transport of the plants, and the plants' storage and tolerance of the accumulated metals. Considerably less information is available on the processes in the rhizosphere of hyperaccumulators. Root proliferation and effective root uptake mechanisms are among the key processes in the rhizosphere that distinguish metal hyperaccumulators from normal plants. The roles of root exudates and microbial activity in the soil are largely unknown, although Zhao et al. (2001) has recently suggested that root exudates of the genus of plants from *Thlaspi* do not enhance mobilization of metals in soil.

Microorganisms (also called microbes) are usually present in soils to which hyperaccumulators are native, even in those soils containing high concentrations of metals. Microorganisms (such as bacteria) in the soil may affect trace metal mobility and availability to the hyperaccumulator plant; they may produce iron chelators and siderophores for ensuring iron availability, reduce soil pH, and/or solubilize metal-phosphates. For example, chemolithotrophic bacteria have been shown to enhance environmental mobility of metal contaminants via soil acidification, or in contrast, to decrease their solubility due to precipitation as sulfides. Some microbes influence root parameters, such as root morphology and growth. An increase in root exudation of organic solutes could affect the rate of phytosiderophore release. In turn, rhizosphere microorganisms may interact symbiotically with roots to enhance the potential for metal uptake.

Any practice that increases metal (such as Ni) uptake into plants during phytomining would increase the commercial value of using metal-extracting plants, particularly hyperaccumulators, and thus the ultimate success of phytomining and phytoremediation.

SUMMARY OF THE INVENTION

Figure 1:
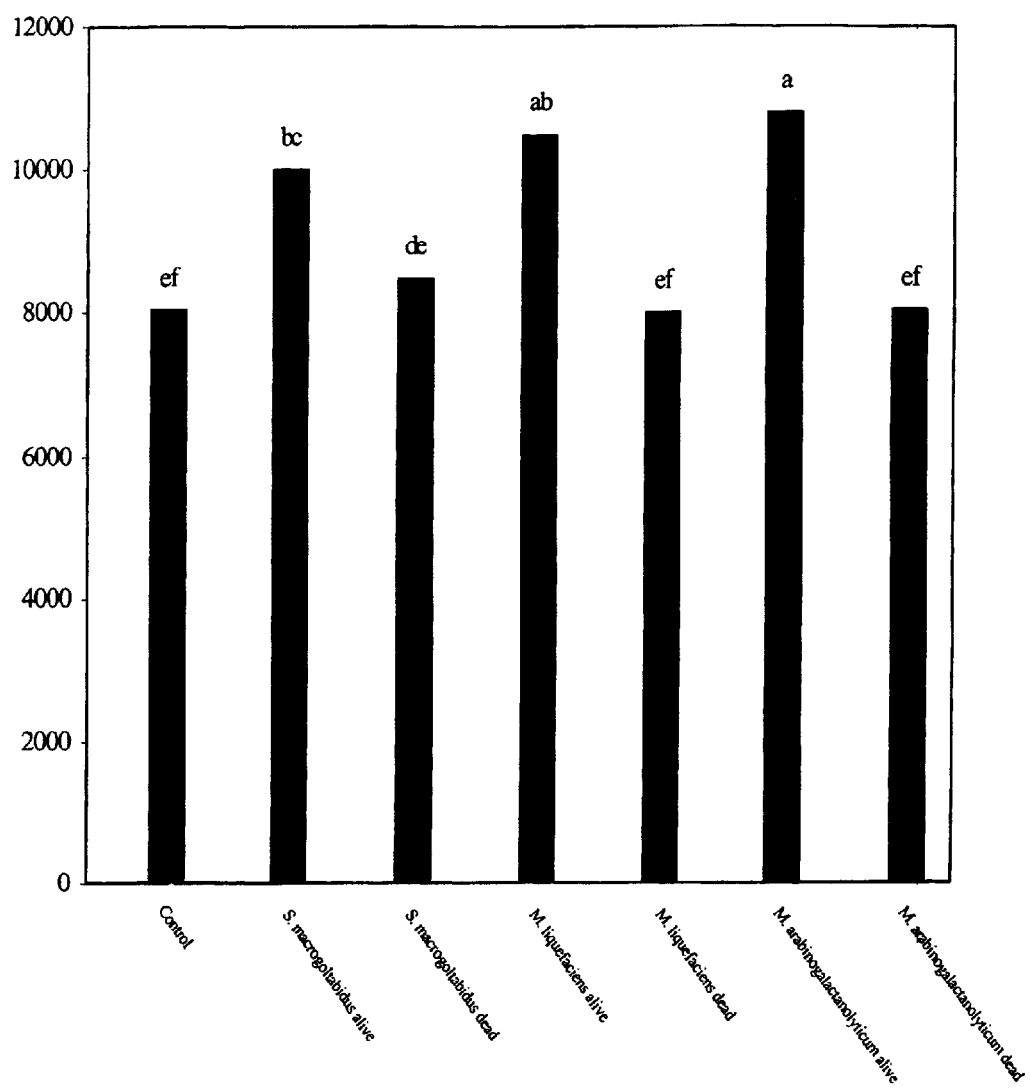
FIG. 1 illustrates the effect of bacterial inoculation regarding Ni uptake.

The present invention relates to methods for enhancing the ability of plants to extract metals from soil. As used herein, the term "metal-extracting plant" means a plant that can extract metal from soil, and includes hyperaccumulators. As used herein, the term "enhancing-bacteria" means any microbe that enhances the ability of a metal-extracting plant to extract metal from soil and includes rhizobacteria. Such enhancement means that the metal-enhancing plant extracts more metal from the soil utilizing a method according the invention than it would if the invention were not utilized.

A method according to the invention is preparing soil including metal to be extracted by adding to the soil enhancing-bacteria that enhances the ability of a metal-extracting plant to extract the metal from the soil.

Another method according to the invention is extracting metal from soil, wherein the method comprises the steps of adding an enhancing-bacteria to the soil, and planting one or more metal-extracting plants to the soil to extract the metal, wherein the ability of the metal-extracting plants to extract the metal is enhanced by the presence of the enhancing-bacteria in the soil. Preferably the metal-extracting plants are added to the soil as seeds and preferably the seeds have been inoculated with the enhancing-bacteria.

DETAILED DESCRIPTION OF A PREFERRED EMBODIMENT

The following detailed description is for the purpose of setting forth explemplary embodiments of the invention, and is not meant to limit the scope of the invention. As previously mentioned, some plants, such as *Alyssum murale* ("*A. Murale*"), have a remarkable ability to hyperaccumulate metals, such as Ni, from soils containing mostly nonlabile metals (particularly Ni). The present inventors have found that microbes, particularly certain rhizobacteria, enhance metal accumulation (and hence, extraction) by plants, for example Ni extraction by *A. murale*, and this phenomenon is believed by the inventors to be caused by the ability of the microbes to increase the availability to the plant of metal in soil, although the invention is not limited to any particular theory.

In the example herein, three bacteria, *Sphingomonas macrogoltabidus*, *Microbacterium liquefaciens*, and *Microbacterium arabinogalactanolyticum* were added to both sterile and nonsterile Ni-rich, serpentine soil collected from OR, USA. *Sphingomonas macrogoltabidus* reduced Ni extraction by 10 mM $Sr(NO_3)_2$ from soil. *M. arabinogalactanolyticum* significantly increased Ni extraction, whereas *M. liquefaciens* had no effect except for when plant seeds were inoculated with *M. liquefaciens*. Extractability of few other metals was affected by inoculation of the soil with the enhancing-bacteria (i.e., adding the bacteria to the soil). When these three bacteria were also added to surface-sterilized seeds of *A. murale* grown in nonsterile soil, they increased Ni uptake into the shoot by, respectively, 17% (*S. macrogoltabidus*), 24% (*M. liquefaciens*), and 32.4% (*M. arabinogalactanolyticum*), compared with uninoculated soil controls.

EXAMPLE 1

Soil Sampling and Preparation:

A nickel-rich, serpentine soil was collected near Cave Junction, OR, USA. Samples of this soil were mixed in a large container and dried at room temperature, then were crushed, sieved, and analyzed by the soil testing laboratory of the University of Maryland. Total metals and other physical and chemical properties of the soil are presented in Table 1. One half of the soil was sterilized (at 121° C.) by autoclaving on three separate occasions for 1 hour each time. Table 1 shows the physical and chemical characteristics of this soil:

Bacterial Solubilization of Metals in Soil:

Selecting an enhancing bacterium for use in treating the soil from which metal will be removed is performed by a process involving the step of selecting the microbe by determining whether it will grow in an environment including relatively high concentrations of the metal to be removed from the soil. Other traits that may be used to select the enhancing-bacteria are its ability to: (1) thrive in phosphorus, (2) tolerate low soil pH, and/or (3) produce chelating agents.

Three rhizobacterial strains were selected for study of their effect on Ni extraction from soil and effect on Ni uptake into *A. murale*. These bacteria were originally isolated from the rhizosphere of *A. murale* grown on the same Ni rich, serpentine soil from Oregon, USA. The methods of isolating such bacteria are known to those skilled in the art. A deposit of M. arabingalatanolytcum was made with the American Type Culture Collection (ATCC) on Aug. 21, 2002 on behalf of the University of Maryland and has Patent Deposit Designation PTA4604.

The specific characteristics of the three bacteria selected are as follows: *Sphingomonas macrogoltabidus* is a nonacid producer, non-phosphate solubilizer, nonsiderophore producer, and grows on 8 mM $NiCl_2$. *Microbacterium liquefaciens* is an acid producer, phosphate solubilizer, siderophore producer, and grows on 8 mM $NiCl_2$. *Microbacterium arabinogalactanolyticum* is an acid producer, phosphate solubilizer, nonsiderophore producer, and grows on 8 mM NiCl2.

Bacterial cells were grown overnight in 250-ml Erlenmeyer flasks containing 100 ml of sterilized R2A broth (Reasoner & Geldreich, 1985) on a shaker at 150 r.p.m. at 30° C. until late log phase. Living and dead bacterial cells were then harvested by centrifugation (12 000×g, 20° C., 10 min), and the pellets were washed twice with sterile distilled water. Bacterial suspensions in distilled water were adjusted to an absorbance at 600 nm of 0.5 (equivalent to approximately $7.4 \times 10^8$ CFU $ml^{-1}$). One ml of each bacterial sus-

TABLE I

| Sand | Silt | Clay | OM* | pH | Mg | P | K | Mn | Ca | Zn | Cu | Ni | Cu | CEC*** |
|------|------|------|-----|----|----|----|----|----|----|----|----|----|----|--------|
| | | g $kg^{-1}$ | | | | | | | mg $kg^{-1}$ | | | | | meq100 $g^{-1}$ |
| 48 | 24 | 28 | 4.1 | 6.4 | 172 | 32 | 48 | 37.5 | 178 | 14 | 22 | 4390 | 0.8 | 6.7 |

*Organic matter.
**Cation exchange capacity

Extractable metals were measured by shaking 10 gram, air-dried sterile and nonsterile soil for 2 hours in 20 milliliters of 10 mM $Sr(NO_3)_2$, according to the teachings of Kukier U, Chancy RL. 2001. Amelioration of Ni phytotoxicity in muck and mineral soils, *Journal of Environmental Quality* 30: 1949–1960, the disclosure of which is incorporated herein by reference. Samples were filtered and acidified with $HNO_3$ before analysis. Metal concentrations were determined using both flame atomic absorption spectrometry (AAS), and inductively coupled plasma atomic emission spectrometry (ICP-AES) using yttrium as an internal standard.

pension was used as an inoculum for 10 grams of autoclaved sterile and 10 grams of nonsterile soils in 50 ml Falcon tubes. Soils were incubated at room temperature for 18 days.

Pot Experiment:

First, seeds of *Alyssum murale* were inoculated with a bacteria (i.e., bacteria was added to the seeds). The bacterial cells were grown in 500-ml Erlenmeyer flasks containing 250 ml of sterilized R2A (Reasoner & Geldreich, 1985) broth overnight, until late log phase. Dead cells were obtained by autoclaving at 121 C one flask of each bacterium for 20 minutes. Living and dead bacterial cells were collected as previously described, washed twice with sterile distilled water and then suspended in sterile distilled water. Cell densities were adjusted to an absorbance at 600 nm of 0.5 and were used for seed inoculation.

Before seeding, A. murale seeds were surface-sterilized by shaking in 70% ethanol for 5 min, followed by shaking in 2% sodium hypochlorite for 30 min. Sterile seeds were next washed in five, 5-mm rinses with sterile water.

Surface sterilized A. murale seeds were sown in plastic pots containing 500 g Ni rich serpentine soil mixed with the same volume of perlite. Perlite was added to improve water and gas movement. Five milliliter (ml) of the appropriate bacterial suspension was added at a concentration of $10^8$ Colony Forming Units (CFU) per ml of sterile distilled water, whereas for the noninoculated control plants, just the same amount of sterile distilled water was added. After 2 weeks, the plants were thinned to five plants per pot. Plants were grown for 2 months in a glasshouse at 25° C. and a 16/8 day/night regime, meaning 16 hours of daylight followed by 8 hours of darkness. Tap water and nutrient solutions of $KNO_3(NH_4)_2SO_4$ and $K_2HPO_4/KH_2PO_4$ were added as needed. All treatments were replicated five times.

Plant Harvest and Preparation:

After two months, whole A. murale plants were removed from the pots. Shoot and roots were separated. Plant shoots were washed with deionized water, rinsed and dried at 65° C. Dry plant samples were weighed and ground using a Wiley Mill. Two grams or less were ashed at 480° C. for 16 hours. The ash was digested with concentrated $HNO_3$, dissolved in 3 molar (M) HCl, filtered and diluted to 25 ml with 0.1 M HCl (AOAC Official Method of Analysis 3.014 (a), 1984). Metal concentrations were determined using both MS and inductively coupled plasma atomic emission spectroscopy (ICP-AES) using yttrium as an internal standard.

Statistical Analyses:

Data were analyzed using the Statistical Analysis System ("SAS") version 6.12 (SAS Institute, Cary N.C). Treatment means (i.e., the average of replicates for each bacteria addition) were separated using the Waller-Duncan K-ratio f-test after it was determined that there was a significant (probability or P<0.05) treatment effect using the GLM procedure, which is a statistical method that determines if treatment means are different from one another.

Results:

Peterson (1962) reported that colonization of autoclaved soil by soil microorganisms is inhibited and the duration of inhibition is related to the time of autoclaving and the type of microbe tested. Autoclaving soil destroys the free radical mechanisms involved in biotic transformation of certain organic compounds (Fletcher & Kaufman, 1980). Autoclaving soil has also been shown to influence soil chemistry. Particularly noteworthy is the large increase in extractable Mn, often to toxic levels, that can result from autoclaving soil (Martin et aL., 1973; Skipper & Westermann, 1973; Lopes & Wollum, 1976; Wolf et aL, 1989). Autoclaving soil has also been reported to influence extractable Al and Fe and to decrease trace element levels but generally does not result in significant changes in Ca, Mg, or K levels (Ferriss, 1984).

Soil sterilization significantly reduced $Sr(NO_3)_2$ extractable Ni compared with nonsterilized soils, as shown in Table 2. On the other hand, autoclaving increased extractable Fe, Mn, and Co. Autoclaving had no significant effect on other elements examined. Table 2 shows the effect of autoclaving on extractable metal content using strontium nitrate.

TABLE 2

| Soil | Ni mg kg–1 | Zn dry soil | Cu | Ca | Fe | Mg | Mn | Co | K | P |
|---|---|---|---|---|---|---|---|---|---|---|
| Nonsterile | 2.17[a] | 0.48[a] | <DL | 177.4[a] | 0.01[b] | 114.2[a] | 3.6[b] | 0.00[b] | 21.45[a] | 0.86[a] |
| Sterile | 1.55[b] | 0.47[a] | <DL | 152.6[b] | 0.07[a] | 103.4[a] | 40.7[a] | 0.24[a] | 20.15[a] | 0.99[a] |

<DL = below detection limit.
*Means followed by different letters within the same column are significantly different at P < 0.05.

Thus, in the current study, autoclaving the soil increased extractable soil Mn from 3.6 to 40.7 mg kg$^{-1}$.

To study the influence of the three bacterial isolates on metal solubilization in the serpentine soil, the bacteria were inoculated into sterile and nonsterile soil and extractable metal concentrations were determined at 6 weeks post inoculation. In sterilized soil there were few significant effects of bacterial inoculation on $Sr(NO_3)_2$ extractable concentrations of any of the elements examined, as shown in Table 3. *Microbacterium liquefaciens* significantly increased Fe solubilization and decreased the concentration of extractable Mn in sterile soils compared with the sterile uninoculated soils, as shown in Table 3. *Sphingomonas macrogoltabidus* decreased extractable Ca, Mg, and K. *Microbacterium arabinogalactanolyticum* had no effect on extraction of any of the elements examined. Table 3 shows the effect of different bacterial isolates on metal solubilization in sterilized Ni rich soils.

TABLE 3

| Isolate | Ni mg kg$^{-1}$ | Zn dry soil | Ca | Fe | Mg | Mn | Co | K | P |
|---|---|---|---|---|---|---|---|---|---|
| Control | 1.55[a] | 0.47[a] | 1.52.6[a] | 0.07[b] | 103.4[b] | 40.7[b] | 0.24[b] | 20.2[a] | 0.99[a] |
| S. macro. | 1.63[a] | 0.43[a] | 124.9[b] | 0.06[b] | 80.0[c] | 33.2[bc] | 0.17[b] | 15.1[b] | 0.76[a] |

TABLE 3-continued

| Isolate | Ni mg kg$^{-1}$ | Zn dry soil | Ca | Fe | Mg | Mn | Co | K | P |
|---|---|---|---|---|---|---|---|---|---|
| M. liq. | 1.39$^a$ | 0.50$^a$ | 151.1$^a$ | 0.24$^a$ | 90.7$^b$ | 28.1$^c$ | 0.20$^b$ | 19.5$^a$ | 0.47$^a$ |
| M. arab. | 1.65$^a$ | 0.51$^a$ | 148.8$^a$ | 0.12$^{ab}$ | 113.7$^a$ | 47.5$^a$ | 02.9$^a$ | 17.7$^a$ | 0.32$^a$ |

S. macro., Sphingomonas macrogoltabidus;
M. liq., Microbacterium liquefaciens;
M. arab., Microbactrium arabinogalactanolyticum.
*Means followed by different letters within the same column are significantly different at P < 0.05.

In nonsterile soil, *Microbacterium arabinogalactanolyticum* increased Ni extractability but had no effect on any other elements examined. The concentration of extractable Ni was increased from a control of 2.2 mg kg$^{-1}$ to 2.6 mg kg$^{-1}$ when the soil was inoculated with *M. arabinogalactanolyticum*. *Sphingomonas macrogoltabidus* decreased the amount of Ni and K extracted from soil, as shown in Table 4. *Microbacterium liquefaciens* had no effect on Ni extraction in this test, but was shown to increase extraction of Fe, Mn and Co. Table 4 shows the effect of different bacterial isolates on metal solubilization in nonsterilized Ni rich soils.

TABLE 4

| Isolate | Ni mg kg$^{-1}$ | Zn dry soil | Ca | Fe | Mg | Mn | Co | K | P |
|---|---|---|---|---|---|---|---|---|---|
| Control | 2.2$^b$ | 0.48$^a$ | 177.4$^a$ | 0.012$^b$ | 114.2$^{ab}$ | 3.6$^{bc}$ | 0.000$^b$ | 21.4$^a$ | 0.85$^a$ |
| S. macro. | 1.7$^c$ | 0.50$^a$ | 17.14$^a$ | 0.001$^b$ | 103.3$^b$ | 0.08$^c$ | 0.002$^b$ | 16.7$^b$ | 0.46$^a$ |
| M. liq. | 1.9$^{bc}$ | 0.53$^a$ | 162.5$^a$ | 0.312$^a$ | 10.35$^b$ | 16.3$^a$ | 0.106$^a$ | 23.4$^a$ | 0.87$^a$ |
| M. arab. | 2.6$^a$ | 0.61$^a$ | 163.8$^a$ | 0.000$^b$ | 124.4$^a$ | 5.7$^{bc}$ | 0.000$^b$ | 20.7$^a$ | 0.421$^a$ |

S. macro., Sphingomonas macrogoltabidus;
M. liq., Microbacterium liquefaciens;
M. arab., Microbactrium arabinogalactanolyticum.
*Means followed by different letters within the same column are significantly different at P < 0.05.

It is speculated that acid, siderophore production and/or phosphate solubilization by the enhancing-bacteria facilitated metal solubility in the nonsterile, Ni-rich soils; however, the invention is not limited to any particular theory. Siderophore production can also be stimulated by the presence of heavy metals (as discussed by van der Lelie et al., 1999) and because most siderophores show affinity to bivalent metal ions (Neilands, 1981), they possibly affect bioavailability as well. For instance, it was reported that in *Azobacter vinelandii*, siderophore production is increased in the presence of Zn (II), as discussed by Huyer & Page, 1988. Iron chelating hydroxamic acid production in *Bacillus megaterium* is increased by exposure to Cu, Cr, Cd, Zn, and Al (discussed by Beyers et aL, 1967, and by Hu & Boyer, 1996). Zinc, Cd, Ni, and Al were found to increase siderophore production in *Pseudomonas aeruginosa* (Gilis, 1993; Hassan, 1996). The same effect was found for Zn and Al in P. fluorescens ATCC17400 (Gilis, 1993).

Bacterial inoculation on Ni uptake by *A. murale* in sterilized and nonsterilized Ni-rich soils showed that *A. Murale* grown from seeds inoculated with enhancing-bacteria (for example, the bacteria was added to the surface of the seeds) extracted more nickel than seeds that were not inoculated. To study the effect of bacterial inoculation on Ni accumulation in plants grown in nonstenle soil, *S. macrogoltabidus*, *M. liquefaciens* or *M. arabinogalactanolyticum* were added to surface sterilized *A. murale* seeds at the time of sowing. The addition of the bacteria to the seeds significantly increased the Ni uptake of *A. murale* by 17, 24, and 32%, respectively, compared With uninoculated seeds, as shown in FIG. 1. *Microbactenum arabinogalactanolyticum* increased foliar Ni from a control concentration of 8500 mg kg$^1$ to 12 000 mg kg$^{-1}$. *Sphingomonas macrogaltabidus* increased Ni uptake into *Alyssum*, although to a lesser concentration as compared to the control, despite the finding that it actually decreased the concentration of Ni extracted from soil. This demonstrates that plant bioavailability of Ni was affected in a way that did not always affect extraction with a weak acid.

There were no significant effects on uptake when dead bacteria of each isolate were tested as shown in FIG. 1. Further, there were no significant effects bacterial inoculation (dead or living) on shoot dry weight of *A. murale* (data not shown).

Clearly, despite the fact that *Alyssum* hyperaccumulates Ni even without bacteria present in its rhizosphere, adding enhancing-bacteria to the soil helps to increase the extraction of Ni for hyperaccumulation from soils with a high proportion of non-labile Ni. This indicates that the bacteria somehow enhanced the availability of Ni to the plant, which in the preferred embodiment is *A. murale*. A possible explanation might be acid, siderophore production and/or phosphate solubilization although, as previously stated, the invention is not limited to a particular theory. These findings parallel Whiting et al. (2001), who found that the addition of a mixed inoculum of *Microbacterium saperdae*, *Pseudomonas monteili*, and *Enterobacter cancerogenes* to surface sterilized seeds of *T. caerulescens* sown in autoclaved soil increased the Zn concentration in shoots 2-fold compared with axenic controls; the total accumulation of Zn was enhanced 4-fold.

Enhanced uptake of Ni by *A. murale* is important to the overall process of phyroextraction of Ni from soils. As the technology of Ni phytomining matures and is commercially developed, even small increases in Ni uptake can have very significant impacts on profitability.

Having now described a preferred embodiment of the invention, alterations and modifications that do not depart from the spirit thereof may occur to others. The invention is thus not limited to the preferred embodiments but is instead set forth in the appended claims and legal equivalents thereof. Moreover, for any method claimed herein, the steps may be performed in any manner capable of increasing the extraction of metal from soil by a plant. Additionally, use of the indefinite article "a" means "one or more."

What is claimed is:

1. A method of extracting metal from non-sterile soil, the method comprising the steps of adding an enhancing-bacteria to the soil and planting a metal-extracting plant in the soil, wherein the ability of the metal-extracting plant to extract metal present in the soil is enhanced by the presence of the enhancing-bacteria.

2. The method of claim 1 that further includes the step of growing the enhancing-bacteria.

3. The method of claim 1 wherein the metal is nickel.

4. The method of claim 1 wherein the plant is from the genus *Alyssum*.

5. The method of claim 4 wherein the plant is *Alyssum murale*.

6. The method of claim 1 wherein the enhancing-bacteria is one or more of the group consisting of *M. arabinogalactanolyticum* and *M. liquefaciens*.

7. The method of claim 6 wherein the enhancing-bacteria comprises *rhizobacteria*.

8. The method of claim 7 wherein the enhancing-bacteria comprises *M. arabinogalactanolyticum*.

9. The method of claim 7 wherein the enhancing-bacteria comprises *M. liquefaciens*.

10. The method of claim 1 wherein the plants are planted in the soil as seeds.

11. The method of claim 1 wherein the enhancing-bacteria is added to the seeds as well as to the soil.

12. The method of claim 11 wherein the enhancing-bacteria is one or more of the group consisting of *M. arabinogalactanolyticum* and *M. liquefaciens*.

13. The method of claim 11 wherein the enhancing-bacteria comprises *rhizobacteria*.

14. The method of claim 13 wherein the enhancing-bacteria comprises *M. arabinogalactanolyticum*.

15. The method of claim 13 wherein the enhancing-bacteria comprises *M. liquefaciens*.

16. The method of claim 11 wherein the seeds are surface sterilized before the enhancing-bacteria is added to the seeds.

17. The method of claim 11 wherein the seeds are those of *Alyssum murale*.

18. The method of claim 1 wherein the soil includes organic material in addition to the bacteria.

19. The method of claim 1 wherein the soil includes silt.

20. The method of claim 1 wherein the soil includes clay.

21. The method of claim 1 wherein the soil includes sand.

22. The method of claim 1 wherein the soil includes one or more metals from the group consisting of nickel, copper, zinc, potassium, manganese, phosphorus, magnesium and calcium.

23. The method of claim 1 wherein the soil includes at least one of the group consisting of sand, clay, and silt.

24. The method of claim 1 wherein the soil is autoclaved before the plants are planted.

25. The method of claim 1 wherein the plant is a hyperaccumulator.

26. (A method of extracting nickel from soil, the method comprising the steps of adding an enhancing-bacteria to the soil and planting in the soil a metal-extracting plant that is a hyperaccumulator of nickel, wherein the ability of the metal-extracting plant to accumulate nickel is enhanced by the enhancing-bacteria in the soil.

27. The method of claim 26 that further includes the step of growing the enhancing-bacteria.

28. The method of claim 26 wherein the plant is from the genus *Alyssum*.

29. The method of claim 28 wherein the plant is *Alyssum murale*.

30. The method of claim 26 wherein the enhancing-bacteria is one or more of the group consisting of *M. arabinogalactanolyticum* and *M. liquefaciens*.

31. The method of claim 26 wherein the enhancing-bacteria is *rhizobacteria*.

32. The method of claim 31 wherein the enhancing-bacteria comprises *M. arabinogalactanolyticuim*.

33. The method of claim 31 wherein the enhancing-bacteria comprises *M. liquefaciens*.

34. The method of claim 26 wherein the plants are planted in the soil as seeds.

35. The method of claim 34 wherein the enhancing-bacteria is added to the seeds as well as to the soil.

36. The method of claim 26 wherein the enhancing-bacteria is *rhizobacteria*.

37. The method of claim 36 wherein the enhancing-bacteria comprises *M. arabinogalactanolyticum*.

38. The method of claim 36 wherein the enhancing-bacteria comprises *M. liquefaciens*.

39. The method of claim 35 wherein the enhancing-bacteria is selected from one or more of the group consisting of *M. arabinogalactanolyticum* and *M. liquefaciens*.

40. The method of claim 35 wherein the seeds are surface sterilized before the enhancing-bacteria is added to the seeds.

41. The method of claim 35 wherein the seeds are those of *Alyssum murale*.

42. The method of claim 26 wherein the soil includes organic material in addition to the bacteria.

43. The method of claim 26 wherein the soil includes silt.

44. The method of claim 26 wherein the soil includes clay.

45. The method of claim 26 wherein the soil includes sand.

46. The method of claim 26 wherein the soil includes one or more metals from the group consisting of nickel, copper, zinc, potassium, manganese, phosphorus, magnesium and calcium.

47. The method of claim 26 wherein the soil is nonsterile.

48. The method of claim 26 wherein the soil is autoclaved before the metal-extracting plants are planted.

49. The method of claim 26 wherein the plant is a hyperaccumulator.

* * * * *

UNITED STATES PATENT AND TRADEMARK OFFICE
CERTIFICATE OF CORRECTION

PATENT NO. : 7,214,516 B2  
APPLICATION NO. : 10/814788  
DATED : May 8, 2007  
INVENTOR(S) : Jay Scott Angle et al.

Page 1 of 1

It is certified that error appears in the above-identified patent and that said Letters Patent is hereby corrected as shown below:

On the Title Page

Item (73)

Please add the second assignee's name and should read as follows:

-- United States of America as represented by the Secretary of Agriculture --

Signed and Sealed this

Fourteenth Day of October, 2008

JON W. DUDAS  
*Director of the United States Patent and Trademark Office*